United States Patent [19]

Fenyves

[11] Patent Number: 5,103,098
[45] Date of Patent: Apr. 7, 1992

[54] HIGH RESOLUTION GAMMA RAY DETECTORS FOR POSITRON EMISSION TOMOGRAPHY (PET) AND SINGLE PHOTON EMISSION COMPUTED TOMOGRAPHY (SPECT)

[75] Inventor: Ervin J. Fenyves, Dallas, Tex.
[73] Assignee: Board of Regents, The University of Texas System, Austin, Tex.
[21] Appl. No.: 433,617
[22] Filed: Nov. 9, 1989
[51] Int. Cl.$^5$ .............................................. G01T 1/20
[52] U.S. Cl. .................................... 250/368; 250/366; 250/367
[58] Field of Search ......................... 250/368, 367, 366

[56] References Cited

U.S. PATENT DOCUMENTS

| | | |
|---|---|---|
| 3,978,337 | 8/1976 | Nickles et al. ............ 250/367 |
| 4,677,299 | 6/1987 | Wong ..................... 250/363.03 |
| 4,739,168 | 4/1988 | Aoki ..................... 250/368 |
| 4,749,863 | 6/1988 | Casey et al. ............. 250/363.03 |
| 4,823,016 | 4/1989 | Yamashita et al. ......... 250/363.03 |
| 4,829,185 | 5/1989 | Cerff ..................... 250/361 R |
| 4,942,302 | 7/1990 | Koechner ................. 250/368 |
| 4,942,308 | 7/1990 | Koechner ................. 250/368 |
| 4,973,845 | 11/1990 | Mastrippolito et al. ...... 250/368 |

FOREIGN PATENT DOCUMENTS

| | | |
|---|---|---|
| 377825A2 | 7/1990 | European Pat. Off. . |
| 57-76466 | 5/1982 | Japan ..................... 250/368 |
| 60-159675 | 8/1985 | Japan . |
| 2198620A | 6/1988 | United Kingdom . |
| 8504959 | 11/1985 | World Int. Prop. O. ...... 250/367 |

OTHER PUBLICATIONS

Uchida, et al, "Design of a Mosaic BGO Detector System for Positron CT," IEEE Transactions on Nuclear Science, vol. 33, No. 1, pp. 464–467, Feb. 1986.
Chaney, "Monte Carlo Simulation of Gamma Ray Detectors Using Scintillation Fibers," SPIE vol. 1159 EUV, X-Ray, and Gamma-Ray Instrumentation for Astronomy and Atomic Physics, pp. 18–26, 1989.
Atac, et al, "High Resolution Gamma-Ray Telescopes and Medial Imagers Using Scintillating Fibers and Position Sensitive Photomultipliers," SPIE vol. 1161, New Methods in Microscopy an Low Light Imaging, pp. 178–188, 1989.
Atac, et al, "High Resolution Gamma Ray Telescope Using Scintillating Fibers and Position Sensitive Photomultipliers," Nuclear Physics B, pp. 139–142, 1989.
Atac, et al, "A High Resolution Scintillating Fiber Gamma-Ray Telescope," Proc. First International Sympsium on the Super Collider, pp. 699–707, Feb., 1989.
Fenyves, "Space-Based High Resolution Gamma-Ray Telescope," SPIE vol. 879, Sending, Discrimination, & Signal Processing & Superconducting Materials & Instrumentation, pp. 29–36, 1988.

(List continued on next page.)

Primary Examiner—Constantine Hannaher
Attorney, Agent, or Firm—Arnold, White, Durkee

[57] ABSTRACT

A device and method for detecting gamma rays in a diagnostic imaging system preferably utilizing fast step index scintillating fibers and photomultipliers is provided by the present invention. A plurality of scintillating fibers are formed into layers comprising substantially parallel fibers positioned lengthwise each other in each layer. Each layer is positioned parallel each adjacent layer with each layer having its respective fibers at an angle of substantially either 60° or 90° to each adjacent layer. Preferably, position sensitive photomultipliers are provided and each photomultiplier is coupled to a plurality of fibers and each fiber has at least one end coupled to a photomultiplier. Data output from each photomultiplier is collected and processed to determine spatial coordinates of the origination position of a detected gamma ray. The present invention provides a high resolution gamma ray detector having an improved signal-to-noise ratio. This improves significantly the diagnostic power of the presently used PET and SPECT systems, and greatly extends the field of their application both in medical diagnosis and research. In addition, the present invention enables use of longer-lived positron emitting radioactive isotopes than presently used in typical PET systems.

23 Claims, 5 Drawing Sheets

OTHER PUBLICATIONS

Petroff et al, "High Energy Particle Tracking Using Scintillating Fibers and Solid State Photomultipliers," IEEE Transactions on Nuclear Science, vol. 36, No. 1, pp. 163–164, Feb., 1989.

Buschsbaum et al, "Functional and Anatomical Brain Imaging: Impact on Schizophrenia Research," Schizophrenia Bulletin, vol. 13, No. 1, pp. 115–132, 1987.

Bower, "Images of Obsession," Science News, vol. 131, pp. 236–237, Apr. 11, 1987.

Lancaster et al, "Computers, Physics, and Medicine: Imaging the Body," Computers in Physics, pp. 16–22, Sep.–Oct., 1988.

Langham, "PET Scanning, Earlier and Better Pictures of Disease," Texas Times, pp. 42–45, Winter, 1985.

Andreasen, "Brain Imaging: Applications in Psychiatry," Science, vol. 239, pp. 1381–1388, Mar. 18, 1988.

Brownell et al, "Positron Tomography and Nuclear Magnetic Resonance Imaging," Science, vol. 215, pp. 619–626, Feb. 5, 1982.

Blumenfeld et al, "Plastic Fibers in High Energy Physics," Nucl. Inst. and Meth. in Phys. Res., A 257, 603–606, 1987.

HIGH RESOLUTION GAMMA RAY DETECTORS FOR POSITRON EMISSION TOMOGRAPHY (PET) AND SINGLE PHOTON EMISSION COMPUTED TOMOGRAPHY (SPECT)

BACKGROUND OF THE INVENTION

1. Field of the Invention

This invention relates to a device and a method for accurately locating the origination position of a gamma ray in a diagnostic imaging environment.

2. Description of Related Art

Recent advances in diagnostic imaging, such as magnetic resonance imaging (MRI), computerized tomography (CT), single photon emission computerized tomography (SPECT), and positron emission tomography (PET) have made a significant impact in cardiology, neurology, oncology, and radiology. Although these diagnostic methods employ different techniques and yield different types of anatomic and functional information, this information is often complementary in the diagnostic process.

Generally speaking, PET involves the detection of gamma rays in the form of annihilation photons from short-lived positron emitting radioactive isotopes including, but not limited to $^{18}F$ with a half-life of approximately 110 minutes, $^{11}C$ with a half-life of approximately 20 minutes, $^{13}N$ with a half-life of approximately 10 minutes and $^{15}O$ with a half-life of approximately 2 minutes, using the coincidence method. These radiotracers or radiopharmaceuticals typically are synthesized from labeled precursors and are inhaled or injected into the patient.

Typical PET scanners or tomographs consist of banks of large numbers of scintillation detectors surrounding the patient and are coupled to complex computerized data acquisition systems. The images of the temporal and spatial distributions of the inhaled or injected radiopharmaceuticals are reconstructed by using mathematical imagery construction techniques similar to those applied in computerized tomography. PET provides unique functional information on blood flow and metabolism not easily obtainable by other technologies. Because of the short half-lives of the isotopes used, they are typically produced in an on-site cyclotron or other type of particle accelerator.

SPECT, on the other hand, uses longer-lived isotopes including but not limited to $^{99m}Tc$ with a half life of approximately 6 hours and $^{201}Tl$ with a half life of approximately 74 hours. However, the resolution in present SPECT systems is even lower than that presently available in PET systems.

Typical detectors in presently available PET and SPECT systems comprise inorganic scintillators, such as sodium iodine or bismuth germanate scintillators. These scintillators typically offer a resolution of about 1 centimeter (cm) or slightly better. Further, inorganic scintillators can produce pile-up problems, when multiple events occur within a brief period of time within the scintillator due to the slow time resolution of the scintillator. An event comprises the interaction of a particle, including but not limited to a gamma ray, with the scintillator producing photons within the scintillator. A fraction of the photons produced within a scintillator reach a photon detector coupled to the scintillator where they are counted.

Present PET and SPECT systems, due to their limited resolution, are unlikely to show the beginning of blockage in an artery approximately one-half centimeter wide. Similarly, where an isotope injected in a patient attaches to a tumor, presently available systems are typically able to locate the tumor only to an approximate degree of accuracy of about 1 centimeter or slightly better. Particularly where such a tumor is positioned in a sensitive area, such as a brain, a higher spatial resolution system would be desirable to allow more precise location of the tumor. Similarly, increased resolution in PET and SPECT systems could allow for detection of early stages of potential artery blockage along with other benefits generally resulting from improved imaging.

SUMMARY OF THE INVENTION

Generally speaking, the present invention provides an imaging system offering high spatial and time resolution.

A device of the present invention for detecting a gamma ray in a diagnostic imaging system largely solves the problems associated with known detection devices by providing general improvements in spatial resolution, time resolution and scanner sensitivity in PET and SPECT system environments. Broadly speaking, the device of the present invention comprises a plurality of scintillating fibers, including but not limited to fast step index scintillating fibers, positioned to receive gamma rays from a gamma ray source, a plurality of photomultipliers coupled to these scintillating fibers, and a system for collecting and processing data from the photomultipliers to locate the source of the detected gamma ray. The scintillating fibers preferably comprise at least one scintillating fiber stack. The stack comprises a plurality of layers of scintillating fibers and each layer comprises a plurality of scintillating fibers positioned lengthwise, substantially parallel and immediate each adjacent fiber within the same layer. Each layer preferably being one fiber diameter in depth and being positioned parallel each adjacent layer. Further, fibers in each layer are positioned at an angle to the fibers in each adjacent layer. This angle is referred to as the interlayer fiber angle.

In a preferred embodiment, a plurality of fiber stacks are positioned about the gamma ray source. This positioning enables detection of gamma rays emitted in multiple directions from the gamma ray source.

In a preferred embodiment, the interlayer fiber angle is 90°. In another preferred embodiment, the interlayer fiber angle is 60° and the plurality of layers comprises at least three layers.

Preferably, each fiber stack is positioned immediate and between two layers of inorganic scintillator material. The layers of scintillator material preferably being substantially parallel to the fiber layers.

Each photomultiplier of the present invention is coupled to at least one fiber and preferably, to a plurality of fibers. Preferably, each fiber has at least one end coupled to one of the photomultipliers. In a preferred embodiment, the photomultipliers of the present invention are position sensitive photomultipliers.

The collecting and processing system of the present invention preferably comprises the outputs from each photomultiplier connected to the inputs of fast analog-to-digital converters, the outputs of the analog-to-digital converters connected to at least one processor, and the processor enabling storage and display of a form of the data. The form of the data stored or displayed may be either processed or raw data. Further, the collecting and processing system enables determination of the spatial coordinates, i.e., the x-y-z coordinates, of the origination position of the detected gamma ray.

The method of the present invention for detecting a gamma ray in a diagnostic imaging system comprises the steps of configuring a plurality of scintillating fibers proximate a gamma ray source, coupling a plurality of photomultipliers to the scintillating fibers, and collecting and processing data output from the photomultipliers to locate the gamma ray source. In a preferred embodiment, the step of configuring the scintillating fibers comprises arranging the fibers in a plurality of layers, positioning a portion of the fibers substantially parallel and lengthwise each other in each layer, and further positioning each layer parallel each adjacent layer in a stack, fibers in each layer being at an angle, the interlayer fiber angle, with respect to the fibers in each adjacent layer. In one preferred embodiment, the interlayer fiber angle is 90°. In another preferred embodiment, the interlayer fiber angle is 60° and the plurality of layers comprises at least three layers.

In a preferred embodiment the step of configuring the fibers further comprises positioning a plurality of fiber stacks about the gamma ray source. This positioning enables detection of gamma rays emitted in multiple directions from the gamma ray source.

Preferably, the step of configuring the fibers further comprises positioning each fiber stack immediate and between two layers of inorganic scintillator material. The layers of scintillator material being substantially parallel to the fiber layers.

In a preferred embodiment, each photomultiplier is coupled to at least one fiber and preferably to a plurality of fibers, and each fiber has at least one end coupled to one of the photomultipliers.

The step of collecting and processing data preferably comprises connecting an output from each photomultiplier to an input of a fast analog-to-digital converter and further connecting an output of each analog-to-digital converter to at least one processor, the processor enabling storage and display of a form of the data.

A further method of determining the spatial coordinates of an origination position of a gamma ray comprises configuring a plurality of scintillating fibers in a plurality of layers, positioning a portion of the fibers substantially parallel and lengthwise each other in each layer, further positioning each layer parallel each adjacent layer, each layer having its respective fibers at an angle to each adjacent layer, coupling a plurality of photomultipliers to the scintillating fibers, each photomultiplier is coupled to at least one fiber and preferably to a plurality of fibers, and each fiber has at least one end coupled to one of the photomultipliers, and collecting and processing data output from the photomultipliers and determining the spatial coordinates of an origination position of a detected gamma ray.

DETAILED DESCRIPTION OF THE PREFERRED EMBODIMENT

1. General Principles

In positron emission tomography (PET) systems presently in use, radiotracers and radiopharmaceuticals are synthesized from labeled precursors and are inhaled or injected into a patient. Radioactive isotopes including but not limited to $^{18}F$, $^{11}C$, $^{13}N$ and $^{15}O$, are typical of the short-lived positron emitting radioactive isotopes used in these radiotracers and radiopharmaceuticals. Because of the short lives, present PET facilities typically have on-site cyclotrons to produce the isotopes. The need for a cyclotron dramatically increases the cost of utilizing a PET system and limits the number of PET systems in place.

The present invention, through the use of scintillating fibers, including but not limited to fast step index scintillating fibers, provides time resolutions which reduce pile-up problems associated with traditional scintillator detectors. Relatively long-lived positron emitting radioactive isotopes, such as Cu-64 and Mn-52 having approximately 12.8 hr. and 5.6 day half-lives respectively, often produce pile-up problems in traditional scintillator detectors. The use of scintillating fibers in the present invention enables the use of long-lived isotopes. The long-lived isotopes generate, in addition to positrons, a significant background of single gamma rays and could not be used efficiently with previously developed detectors having lower resolution mainly because of the poor signal-to-noise (coincidence to background) ratio. Application of these long-lived isotopes is enabled by the present invention and can make PET imaging possible for medical centers which have no cyclotron facilities and obtain their radioactive isotopes from other, distant institutions.

Figure 1A:
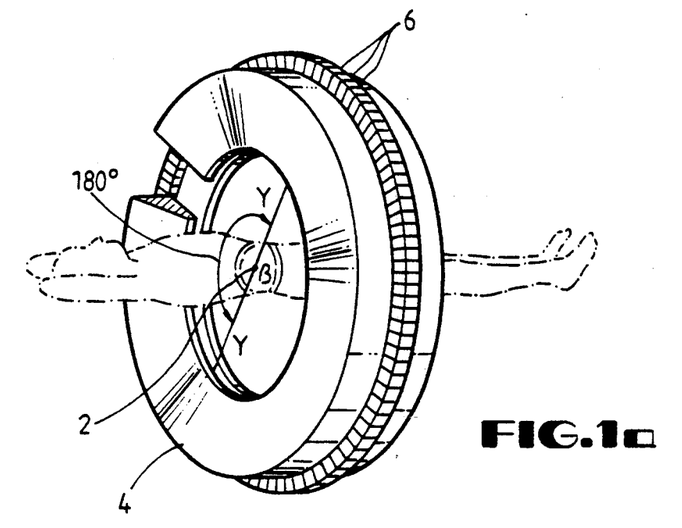
FIG. 1(a) is a perspective drawing of a ring of gamma ray detectors in accordance with the present invention in a PET configuration.

PET scanners typically consist of banks of large numbers of detectors surrounding the patient coupled to computerized data acquisition systems. Referring to FIG. 1(a), the patient having received gamma ray source 2 is positioned within support ring 4. In a preferred embodiment of the present invention, scintillating fiber stacks 6 are positioned about the patient on support ring 4.

The radiotracer or radiopharmaceutical emits a positron which, after travelling a short distance from the nucleus, interacts with a negative electron. The resulting annihilation, yields two approximately 0.51 million electron volt (MeV) photons which are oppositely directed. In other words, the photons resulting from the pair annihilation fly off at 180° from one another.

Figures 1B, 1C:
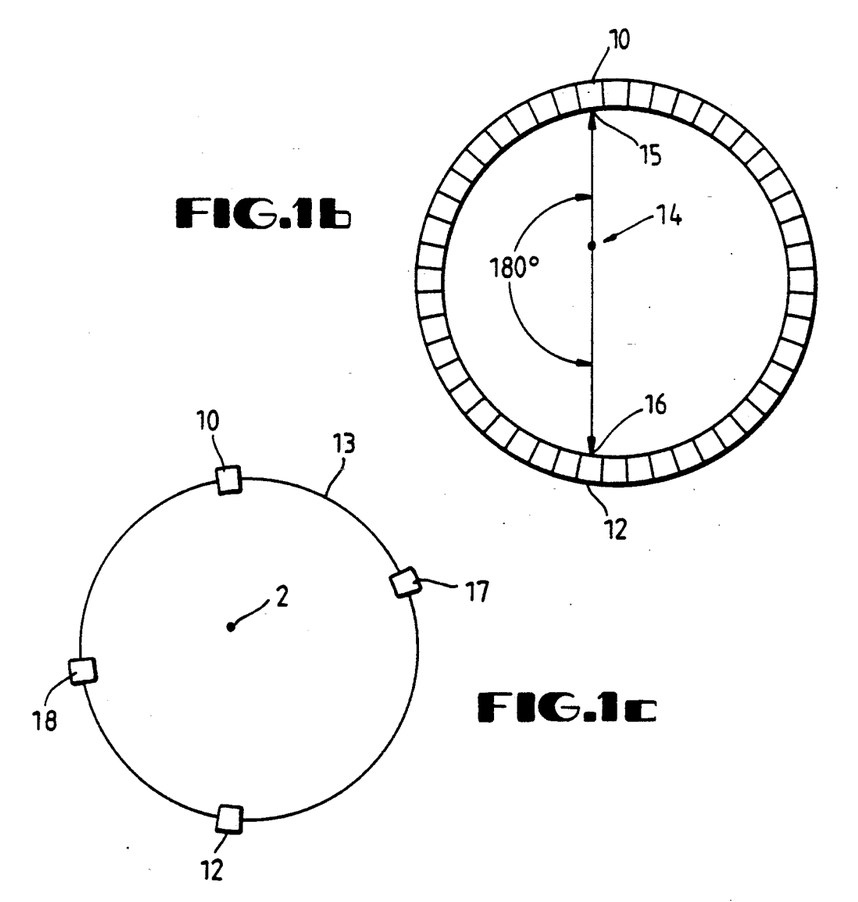
FIG. 1(b) illustrates a technique for locating an origination position of a gamma ray pair in accordance with the present invention in a PET detector.
FIG. 1(c) illustrates another technique for locating an origination position of a gamma ray pair in accordance with the present invention in a PET detector.

FIG. 1(b) illustrates the spatial origination position of gamma ray 14, i.e., the position of the pair annihilation. The gamma ray photons, referred to as gammas, resulting from annihilation fly off at 180° from each other. Gamma 15 strikes scintillating fiber stack 10 and gamma 16 strikes scintillating fiber stack 12. By determining the two points where the gammas strike fiber stacks 10 and 12, knowing the time of flight of a gamma, and knowing the time difference between the striking of the fiber stacks by gammas 15 and 16, the origination position of the gammas can be calculated. In a preferred embodiment, a photomultiplier enables, through a trigger signal, the detection of a gamma.

Referring to FIG. 1(c), in another preferred embodiment, scintillating fiber stacks 10, 12, 17, 18 are positioned about gamma ray source 2 on support 13 enabling fiber stacks 10, 12, 17, 18 to receive gamma rays from gamma ray source 2 to determine the position of the source.

Figure 2:
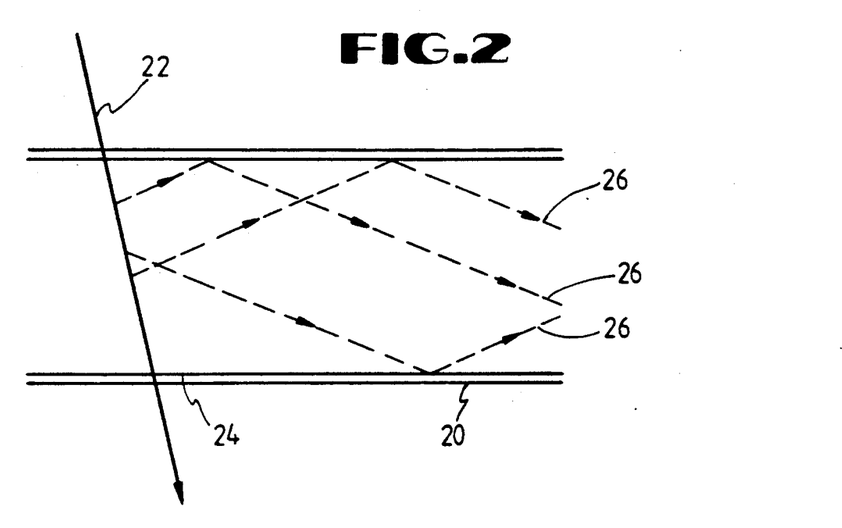
FIG. 2 illustrates a gamma ray passing through a scintillating fiber of the present invention and producing photons in the scintillating fiber.

Referring to FIG. 2, a single scintillating fiber 20 is illustrated. As used throughout this application, the terms fiber and scintillating fiber refer to a scintillating fiber. Scintillating fibers are presently available, by way of example, from Optectron of France and Bicron Corporation of Newburgh Heights, Ohio.

An ionizing particle, including but not limited to a secondary electron generated by gamma ray 22, enters and may pass completely through scintillating fiber 20. Photons 26 are produced within scintillating fiber 20 by scintillation. In a preferred embodiment, scintillating fiber 20 comprises polystyrene doped with butyl-PBD (phenyl-biphenyl-oxadiazole) and POPOP (diphenyloxazolyl-benzene) and is preferably clad in PMMA (polymethylmetacrylate), producing 420 nanometer wavelength photons. The attenuation length of the photons in the fibers is sufficient to allow photons to strike photon detectors coupled to at least one end of the fiber.

2. Fiber Stack Having A 90° Interlayer Fiber Angle

Figure 3:
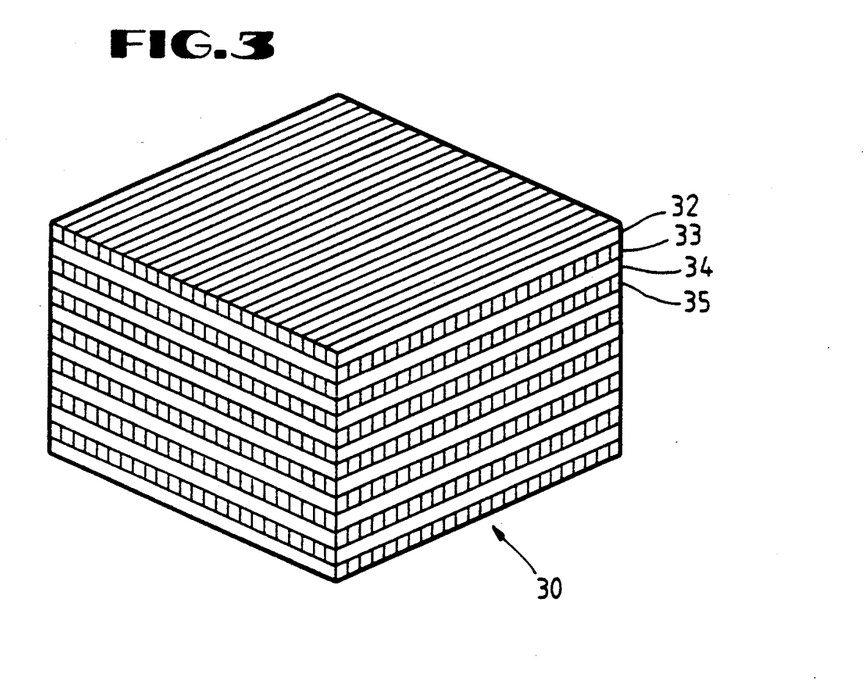
FIG. 3 is a perspective view of a stack of scintillating fibers in accordance with a preferred embodiment of the present invention.

Referring to FIG. 3, a portion of fiber stack 30 is illustrated. Fiber layer 32 comprises lengths of scintillating fibers positioned lengthwise parallel additional lengths of scintillating fibers and forming a layer of scintillating fibers preferably having a depth of the diameter of a single fiber. Fiber layers 32, 33, 34 and 35 are produced in this manner. In this preferred embodiment, the fibers comprising layer 32 are positioned at a 90° angle to the fibers comprising layer 33. Layers 32 and 33 are positioned parallel and immediate each other. Similarly, fibers of layer 34 are positioned at a 90° angle to the fibers of layer 33 and the fibers of layer 35 are positioned at a 90° to the fibers of layer 34. Layers 32, 33, 34 and 35 are positioned parallel and immediate each other. Additional layers are preferably added to the stack as shown in FIG. 3 wherein each layer has its respective fibers positioned at a 90° angle to the fibers of each adjacent layer.

Figure 4:
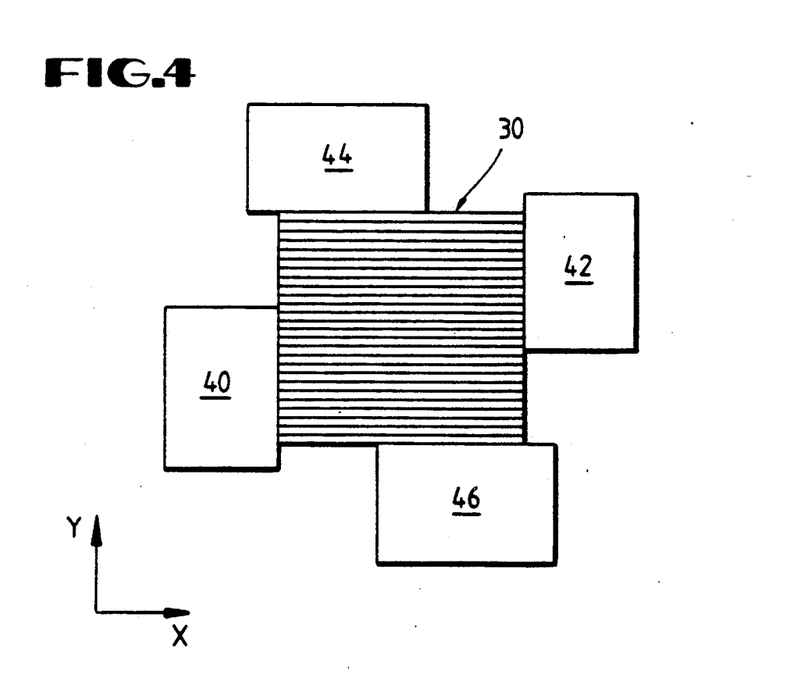
FIG. 4 is a top view of the stack of scintillating fibers of FIG. 3 coupled to photomultipliers in accordance with the present invention.

By way of example, FIG. 4 shows a top view of fiber stack 30 with photon detectors positioned about and coupled to fibers in fiber stack 30. In particular, each fiber in fiber stack 30 is coupled to at least one photon detector. In this preferred embodiment, the photon detectors comprise position sensitive photomultiplier tubes 40, 42, 44, 46. Position sensitive photomultipliers are presently available, by way of example, from Hamamatsu of Japan as part of Hamamatsu's R2486 series.

Preferably, at least one end of each fiber of fiber stack 30 is coupled to a photon detector. As shown in FIG. 4, photomultiplier tubes 40 and 42 are coupled to ends of fibers lengthwise positioned in the x direction. Photomultiplier tubes 44 and 46 are coupled to ends of lengthwise fibers positioned in the y direction. A single position sensitive photomultiplier may be coupled to multiple layers of fibers.

In another preferred embodiment of the present invention, the fiber stack is sandwiched between two thin layers of plastic inorganic scintillator material. The inorganic scintillator material aids in rejecting cosmic rays and other background tracks. Preferably, the inorganic scintillator material is of a thickness approximately in the range of 4 to 10 millimeters.

3. Fiber Stacks Having A 60° Interlayer Fiber Angle

Figure 5:
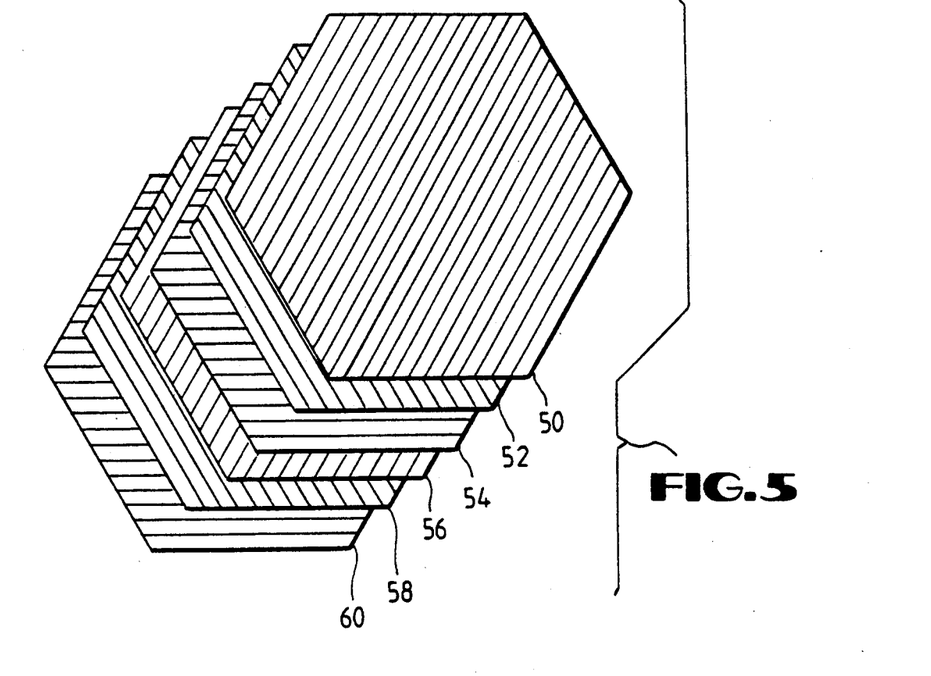
FIG. 5 is a partial, exploded view of a stack of scintillating fibers in accordance with another preferred embodiment of the present invention.

By way of further example, FIG. 5 shows layers of lengthwise parallel fibers 50, 52, 54, 56, 58, 60. Each layer preferably comprises lengths of scintillating fibers positioned lengthwise parallel each other. Each layer preferably is one fiber diameter in thickness. Layer 52 is positioned parallel to layer 50. Layer 52 is positioned having its lengthwise parallel fibers at an angle of substantially 60° to the parallel fibers in adjacent layer 50. Layer 54 is positioned parallel to layer 52. Layer 54 has its lengthwise parallel fibers positioned at substantially a 60° angle to the parallel fibers of layer 52. The process is repeated in layers 56, 58 and 60 wherein each layer is positioned having its parallel fibers at substantially a 60° angle to the fibers in each adjacent layer. A plurality of these layers is preferably formed into fiber stack 64 shown in FIG. 6. FIG. 5 illustrates only a portion of fiber stack 64. Fiber stack 64 comprises a plurality of layers and the six layers shown in FIG. 5 are merely illustrative of the relative positioning of fiber layers in fiber stack 64.

Figure 6:
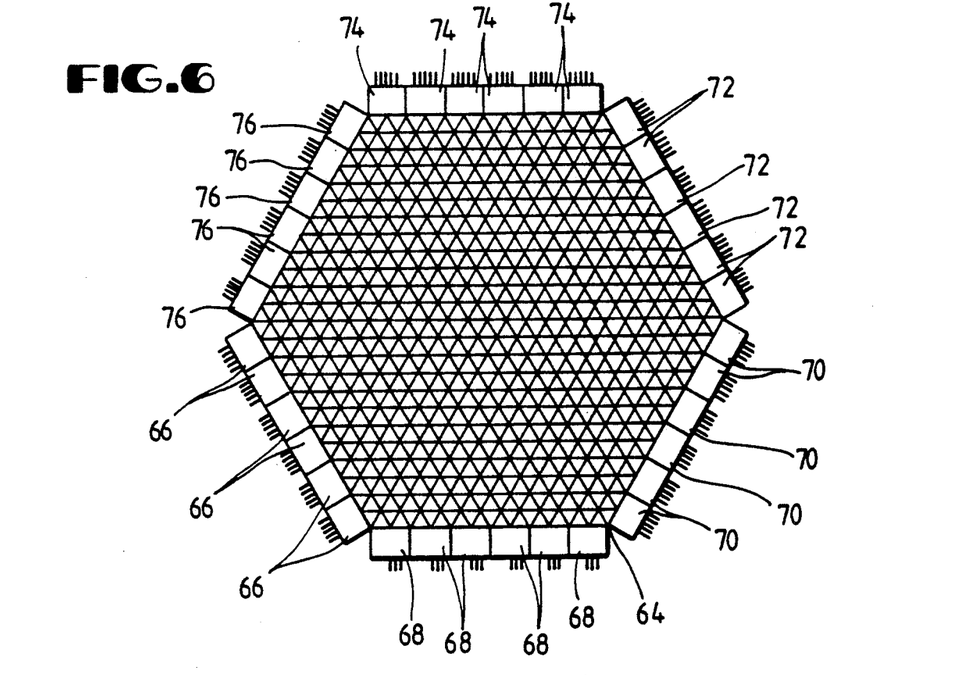
FIG. 6 is a top, schematic view of the stack of scintillating fibers of FIG. 5 coupled to photomultipliers in accordance with the present invention.

By way of still further example, FIG. 6 shows sets of position sensitive photomultiplier tubes 66, 68, 70, 72, 74, 76 coupled to scintillating fibers in each layer of fiber stack 64. At least one end of each scintillating fiber is preferably coupled to a photomultiplier tube. Photomultipliers 66 and 68 are coupled to one end of the parallel fibers in a first fiber layer in fiber stack 64. Photomultipliers 70 and 72 are coupled to parallel fibers in a second layer in fiber stack 64. Photomultipliers 74 and 76 are coupled to parallel fibers in a third layer of fiber stack 64. Additionally, each position sensitive photomultiplier is preferably also coupled to one end of fibers positioned in additional fiber layers where the additionally coupled fiber layers have their fibers parallel to other layers to which the photomultiplier is coupled.

Figure 8:
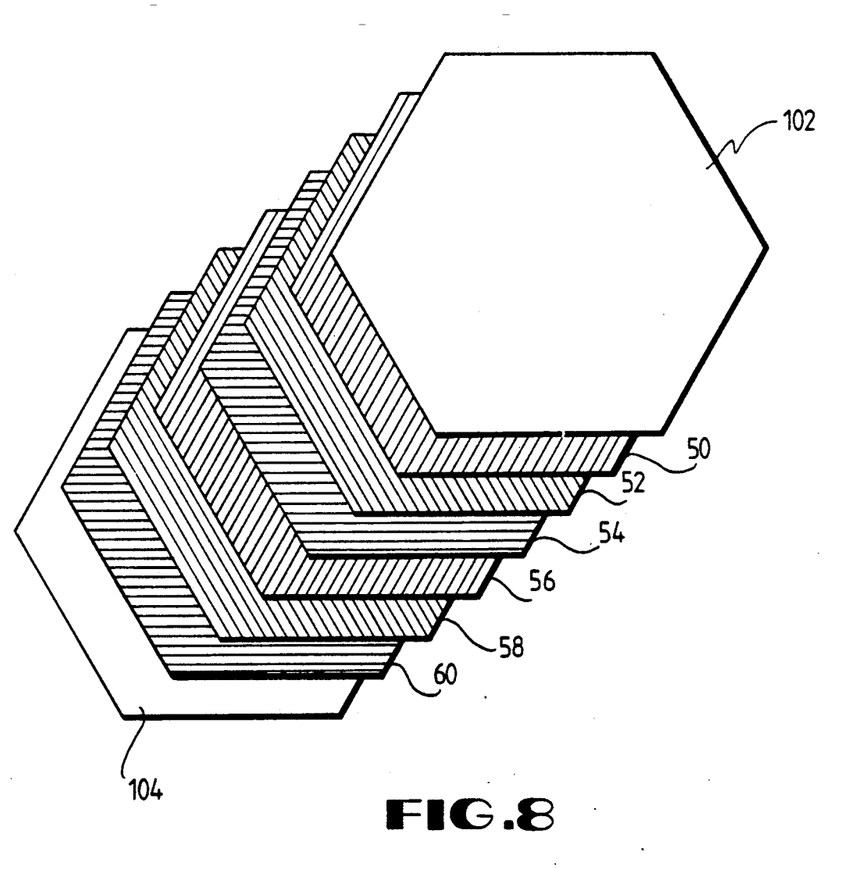
FIG. 8 is a partial, exploded view of a stack of scintillating fibers sandwiched between layers of inorganic scintillator material, in accordance with another preferred embodiment of the present invention.

In another preferred embodiment of the present invention, shown in FIG. 8 the fiber stack including layers 50, 52, 54, 56, 58 and 60 is sandwiched between two thin layers of plastic inorganic scintillator material 102 and 104. The inorganic scintillator material 102 and 104 aid in rejecting cosmic rays and other background tracks. Preferably the layers of inorganic scintillator material 102 and 104 are of a thickness approximately in the range of 4 to 10 millimeters.

4. Data Acquisition System

Figure 7:
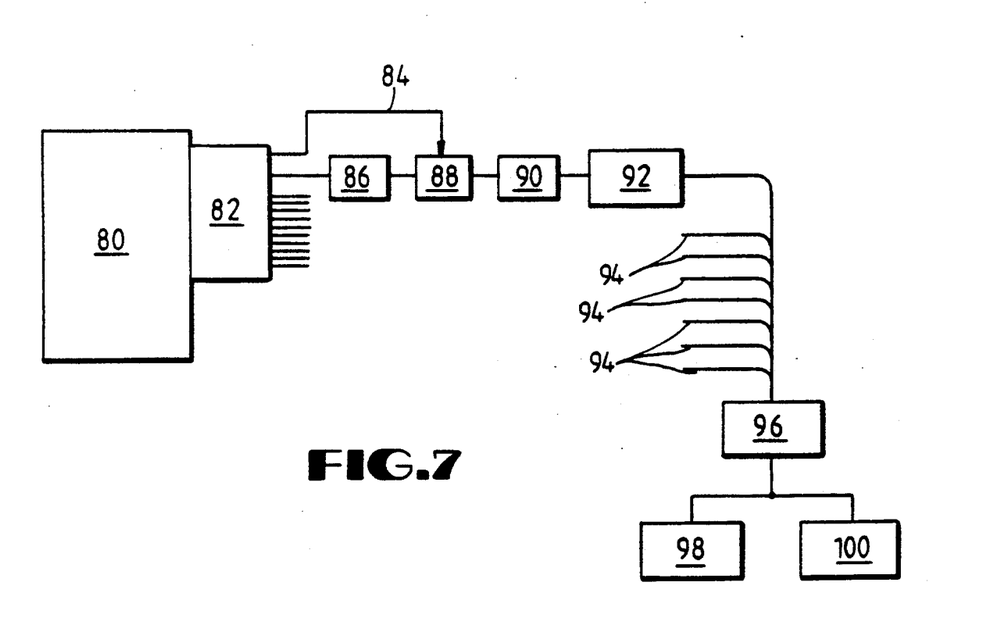
FIG. 7 is a schematic diagram of a system for collecting and processing data in accordance with the present invention.

Referring to FIG. 7, a typical data acquisition system connected to an output related to a position on the face of a position sensitive photomultiplier tube is shown. Position sensitive photomultiplier 82 is coupled to a plurality of layers of fiber within fiber stack 80 wherein the fibers in each layer coupled to photomultiplier 82 are substantially parallel. Amplifier 86 increases the signal output received directly from photomultiplier 82. Trigger 84 from photomultiplier 82 indicates to fast analog-to-digital converter 88 that a photon has been detected by photomultiplier 82. Analog-to-digital converter 88 converts the analog output signal from the photomultiplier corresponding to the photon detected into a digital signal. Buffer 90 interconnects analog-to-digital converter 88 with processor 92. Other processors 94 from other output positions on photo-multiplier 82 and other photomultipliers, as appropriate, are input to image processor 96. Data related to the photon detected is storable in data storage 98 or displayable on data display 100 or both. In this preferred embodiment, the form of data stored in data storage 98 is preferably data already processed by image processor 96. However, raw data may be stored in an alternate data storage systems where the alternate data storage system is positioned prior to image processor 96 in the circuit shown.

In particular, the data acquisition system of the present invention constructs an image from the data collected by the scintillating fibers. Similar systems are presently available from, by way of example, Positron Company of Houston, Tex.

5 Operation

In operation, the gamma ray source in the patient emits positrons which, through annihilation, produce gamma ray pairs which fly off at 180° from one another. Referring to FIG. 1(b), fiber stacks 10 and 12 are impacted by gammas 15 and 16 respectively. The gammas striking the fiber generate photons within the scintillation fiber as shown in FIG. 2. A percentage of these photons produced in the fiber are totally reflected within the fiber. In a preferred embodiment, the fibers are directly coupled to position sensitive photomultiplier tubes, therefore, the photomultiplier detects the photons generated in the fiber. The high resolution of the position sensitive photomultipliers coupled to the closely positioned small diameter fibers in the fiber stack enable determination of the spatial position of each fiber detecting a photon.

The position sensitive photomultipliers of the preferred embodiments of this invention comprise a plurality of x and y positioned anode wires to preserve the position of the photoelectrons produced at the photocathode in the photomultiplier. Resolution of the present invention is, in part, a function of the size of each area corresponding to a position defined by the x-y anode wires within the position sensitive photomultiplier and is also a function of the diameter of the scintillating fibers.

For example, in a present preferred embodiment, 0.5×0.5 square millimeter (mm$^2$) cross-sectional area scintillating fibers are utilized in the fiber stacks. These fibers are coupled to position sensitive photomultiplier tubes consisting of 16 x-positioned and 16 y-positioned anode wires corresponding to a sampling area of 3 mm×3 mm on the face of the tube. Position accuracies better than 0.5 mm are obtainable using this position sensitive photomultiplier resulting in a resolution better than 0.5 mm.

This example is not to be read as a limitation on the present invention but merely as a preferred embodiment. The use of higher resolution photon detection devices, such as high resolution solid state photomultipliers or higher resolution position sensitive photomultiplier tubes, and the use of smaller diameter scintillating fibers, will enable one skilled in the art, by benefit of this disclosure, to practice the present invention and to achieve improved resolution from that of the above example.

In a preferred embodiment, a photon detected by the position sensitive photomultiplier results in charge appearing on the anode wires corresponding to the position of the fiber or fibers detecting photons. The data acquisition system performs a centroid reconstruction having a spatial resolution better than the width of the fibers utilizing techniques known in the art, see e.g., G. Hademenos, dissertation proposal, University of Texas at Dallas, 1988, to reconstruct the origination position of the high energy photons that produced the detected photon event.

The present invention enables the use of longer-lived isotopes than used in traditional PET systems due to an improved signal-to-noise ratio in the fibers. In particular, isotopes including but not limited to Cu-64 and Mn-52 may be used.

Because the velocity of the gammas produced during annihilation are known and because the gammas go off at a 180° angle from each other, when the points of impact of the gammas are accurately determined in accordance with the present invention, the spatial origination point of the gammas, as shown in FIG. 1(b), can be accurately determined.

6. Thickness of the Fiber Stack

The probability of detecting an annihilation photon is a function, in part, of the thickness of the fiber stack.

By way of example, in a preferred embodiment of the present invention a fiber stack utilizing fiber layers has an interlayer fiber angle of 90° and dimensions of substantially 10 cm × 10 cm × 10 cm. This stack results in an approximately 30% probability of detecting gammas used in PET and SPECT devices striking the stack. Further, the gammas impacting the fiber stack preferably result in triggering a photomultiplier coupled to an x direction fiber and in triggering a photomultiplier coupled to a y direction fiber where the triggered photomultipliers are separated in the stack at a depth z enabling accurate determination of x, y and z coordinates of the detected gammas.

Further, if photon detectors are positioned at both ends of a fiber, additional noise reduction may be achieved by requiring both detectors to detect an event substantially within the time period necessary for a photon to traverse the length of the fiber. If only one photon detector detects an event, it may be interpreted as noise, while when both detectors detect an event in a fiber substantially within the time period necessary for a photon to traverse the fiber, there is an increased probability that this is a photon event resulting from a high energy photon striking the fiber.

7. Use in SPECT Systems

The present invention is equally applicable in single photon emission computed tomography (SPECT) applications where the detection of photon trajectories is also required. The present invention, in a SPECT environment, enables the substitution of a traditional SPECT detector system with the present invention.

In particular, the instrument resulting from this technology will be capable of displaying high spatial resolution, three-dimensional, time-resolved distributions of radionucleid-tagged agents, and will allow acquisition of images at ultra-high resolution.

8. Conclusion

The present invention enables increased resolution in PET and SPECT systems. Further modifications and alternative embodiments of the apparatus and method of the present invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. A device for detecting and locating sources of gamma rays within a patient in a medical diagnostic imaging system to provide an image of the patient, comprising:
   a plurality of scintillating fibers positioned to receive gamma rays from gamma ray sources within a patient, each of said scintillating fibers having a maximum cross-sectional area of 0.5×0.5 mm$^2$;
   a plurality of position sensitive photomultipliers coupled to said scintillating fibers; and
   means for collecting and processing data from said position sensitive photomultipliers to determine locations of said sources of said gamma rays, and to produce an image of said patient based upon said locations.

2. The device of claim 1 wherein said plurality of scintillating fibers comprises at least one scintillating fiber stack, said stack comprising:
   a plurality of layers of scintillating fibers, each layer comprising a plurality of scintillating fibers lengthwise positioned substantially parallel and immediate each adjacent fiber within the same layer, each said layer being one fiber diameter in depth and being positioned parallel each adjacent layer; and
   fibers in each layer being at an angle to fibers in each adjacent layer.

3. The device of claim 2 further comprising a plurality of said fiber stacks positioned about said gamma ray source.

4. The device of claim 2 wherein the angle between fibers in each adjacent layer is 90°.

5. The device of claim 2 wherein the angle between fibers in each adjacent layer is 60° and said plurality of layers comprises at least three said layers.

6. The device of claim 2 further comprising a first and a second layer of inorganic scintillator material, said fiber stack being positioned immediate and between said first and second layers of scintillator material.

7. The device of claim 2 wherein each said position sensitive photomultiplier being coupled to at least one said fiber and each said fiber having at least one end coupled to one of said position sensitive photomultipliers.

8. The device of claim 1 wherein each said position sensitive photomultiplier being coupled to at least one said fiber and each said fiber having at least one end coupled to one of said position sensitive photomultipliers.

9. The device of claim 1 wherein said collecting and processing data means comprises an output from each said position sensitive photomultiplier connected to an input of a fast analog-to-digital converter, an output of said analog-to-digital converter being connected to at least one processor, said processor enabling storage and display of a form of said data.

10. The device of claim 1 wherein said collecting and processing data means enables determination of a spatial coordinate of an origination position of the detected gamma ray.

11. A device for locating sources of gamma rays within a patient in a medical diagnostic imaging system to produce an image of the patient, comprising:
   a plurality of scintillating fibers positioned to receive gamma rays from gamma ray sources within a patient to be imaged, comprising at least one scintillating fiber stack, each of said scintillating fibers having a maximum cross-sectional area of 0.5×0.5 mm$^2$;
   said stack comprising a plurality of layers of scintillating fibers, each layer comprising a plurality of scintillating fibers lengthwise positioned substantially parallel and immediate each adjacent fiber within the same layer, each said layer being one fiber diameter in depth and being positioned parallel each adjacent layer, and
   fibers in each layer being at an angle to fibers in each adjacent layer; and
   a plurality of position sensitive photomultipliers coupled to said scintillating fibers.

12. The device of claim 11 further comprising a plurality of said fiber stacks positioned about said gamma ray source.

13. The device of claim 11 wherein each said position sensitive photomultiplier being coupled to at least one said fiber and each said fiber having at least one end coupled to one of said position sensitive photomultipliers.

14. A method for locating sources of gamma rays within a patient in a medical diagnostic imaging system to produce an image of the patient, comprising the steps of:
   configuring a plurality of scintillating fibers proximate a patient having gamma ray sources, each of said scintillating fibers having a maximum cross-sectional area of 0.5×0.5 mm$^2$;
   coupling a plurality of position sensitive photomultipliers to said scintillating fibers; and
   collecting and processing data output from said position sensitive photomultipliers to determine locations of said gamma ray sources, and to produce an image of said patient from said locations.

15. The method of claim 14 wherein said configuring step comprises:
   arranging said fibers in a plurality of layers, positioning a portion of said fibers substantially parallel and lengthwise each other in each said layer, and further positioning each said layer parallel each adjacent said layer in a fiber stack, fibers in each said layer being at an angle with respect to fibers in each adjacent layer.

16. The method of claim 15 wherein said configuring step further comprises positioning a plurality of said fiber stacks about said patient.

17. The method of claim 15 wherein said configuring step further comprises positioning each said layer having its respective fibers at a 90° angle to each adjacent said layer.

18. The method of claim 15 wherein said configuring step further comprises positioning each said layer having its respective fibers at a 60° angle to each adjacent said layer and said plurality of layers comprises at least three said layers.

19. The method of claim 15 wherein said configuring step further comprises positioning said plurality of fiber layers immediate, substantially parallel and between a first and second layer of inorganic scintillator material.

20. The method of claim 15 wherein said coupling step comprises coupling each said position sensitive photomultiplier to at least one said fiber and each said fiber having at least one end coupled to one of said position sensitive photomultipliers.

21. The method of claim 14 wherein said coupling step comprises coupling each said position sensitive photomultiplier to at least one said fiber and each said fiber having at least one end coupled to one of said position sensitive photomultipliers.

22. The method of claim 14 wherein said collecting and processing step comprises connecting an output from said position sensitive photomultiplier to an input of a fast analog-to-digital converter and connecting an output of said analog-to-digital converter to at least one processor, said processor enabling storage and display of a form of said data.

23. A method of determining the spatial coordinates of origination positions of gamma rays within patients in a medical diagnostic imaging system to produce images of the patients comprising:

configuring a plurality of scintillating fibers in a plurality of layers proximate a patient, each of said scintillating fibers having a maximum cross-sectional area of $0.5 \times 0.5$ mm$^2$;

positioning a portion of said fibers substantially parallel and lengthwise each other in each layer;

further positioning each layer parallel each adjacent layer and each layer having its respective fibers at an angle to each adjacent layer;

coupling a plurality of position sensitive photomultipliers to said scintillating fibers, each position sensitive photomultiplier being coupled to at least one fiber and each fiber having at least one end coupled to one of said position sensitive photomultipliers; and collecting and processing data output from said position sensitive photomultipliers to determine the spatial coordinates of origination positions of detected gamma rays, and to produce an image of said patient based upon said origination positions.

* * * * *

UNITED STATES PATENT AND TRADEMARK OFFICE
CERTIFICATE OF CORRECTION

PATENT NO. : 5,103,098
DATED : April 7, 1992
INVENTOR(S) : Ervin J. Fenyves

It is certified that error appears in the above-indentified patent and that said Letters Patent is hereby corrected as shown below:

On the title page, item [75] add the following inventors after "Tex."

--; Pietro P. Antich, Richardson, Tex.; Muzaffer Atac, Wheaton, Ill.; and David B. Cline, Los Angeles, Calif.--

Signed and Sealed this

Eighteenth Day of January, 1994

Attest:

BRUCE LEHMAN

Attesting Officer

Commissioner of Patents and Trademarks